United States Patent [19]

Bowers et al.

[11] Patent Number: 5,108,704
[45] Date of Patent: Apr. 28, 1992

[54] MICROFILTRATION APPARATUS WITH RADIALLY SPACED NOZZLES

[75] Inventors: William F. Bowers, Topsfield; Scott P. Fulton, Brookline; Judith A. Thompson, Marblehead; David M. Donofrio, Rockport, all of Mass.; Kert F. Ivie, Spruce Creek, Pa.

[73] Assignee: W. R. Grace & Co.-Conn., New York, N.Y.

[21] Appl. No.: 245,435

[22] Filed: Sep. 16, 1988

[51] Int. Cl.$^5$ .................. G01N 30/02; B01L 11/00; C12M 1/12

[52] U.S. Cl. .................. 422/70; 422/101; 435/311; 435/301; 210/323.1

[58] Field of Search .............. 210/455, 323.1; 422/101, 70; 435/311, 299–301; 436/161

[56] References Cited

U.S. PATENT DOCUMENTS

| | | | |
|---|---|---|---|
| Re. 30,562 | 3/1981 | Park | 435/296 |
| 3,319,792 | 5/1967 | Leder et al. | 210/238 |
| 3,378,347 | 4/1968 | Saravis | 23/253 |
| 3,378,481 | 4/1968 | Saravis et al. | 204/299 |
| 3,389,966 | 6/1968 | Saravis | 23/230 |
| 3,390,962 | 7/1968 | Goldsmith | 23/253 |
| 3,554,704 | 1/1971 | Ushakoff | 23/253 |
| 3,649,464 | 3/1972 | Freeman | 195/140 |
| 3,674,438 | 7/1972 | Shen | 23/253 |
| 3,730,352 | 5/1973 | Cohen et al. | 210/332 |
| 3,757,952 | 9/1973 | Baitsholts et al. | 210/198 |
| 3,785,928 | 1/1974 | Kessler | 195/140 |
| 3,888,770 | 6/1975 | Avital | 210/238 |
| 3,928,203 | 12/1975 | Kremer | 210/198 |
| 3,963,615 | 6/1976 | Plakas | 210/203 |
| 3,990,852 | 11/1976 | Piazzi et al. | 23/253 |
| 4,012,198 | 3/1977 | Finter et al. | 23/253 |
| 4,031,197 | 6/1977 | Marinkovich | 424/1 |
| 4,079,009 | 3/1978 | Seiler et al. | 210/198 |
| 4,090,850 | 5/1978 | Chen et al. | 23/259 |
| 4,111,754 | 9/1978 | Park | 422/101 |
| 4,167,875 | 9/1979 | Meakin | 73/421 |
| 4,246,339 | 1/1981 | Cole et al. | 435/7 |
| 4,304,865 | 12/1981 | O'Brien et al. | 435/240 |
| 4,317,726 | 3/1982 | Shepel | 210/236 |
| 4,427,415 | 1/1984 | Cleveland | 436/57 |
| 4,483,925 | 11/1984 | Noack | 435/293 |
| 4,493,815 | 1/1985 | Fernwood et al. | 422/101 |
| 4,526,690 | 7/1985 | Kiovsky et al. | 210/335 |
| 4,657,867 | 4/1987 | Guhl et al. | 435/284 |
| 4,734,192 | 3/1988 | Champion et al. | 210/335 |
| 4,787,988 | 11/1988 | Bertoncini et al. | 210/808 |
| 4,877,659 | 10/1989 | Vince | 435/301 |
| 4,927,604 | 5/1990 | Mathus et al. | 210/455 |
| 4,956,298 | 9/1990 | Diekmann | 435/311 |

FOREIGN PATENT DOCUMENTS

| | | |
|---|---|---|
| 0131934 | 1/1985 | European Pat. Off. |
| WO86/07606 | 12/1986 | PCT Int'l Appl. |
| WO89/00285 | 1/1989 | PCT Int'l Appl. |
| 1490362 | 11/1977 | United Kingdom |

OTHER PUBLICATIONS

"Laboatory Separation", Amicon, 1987, p. 52.
Isolab Inc. "Microfold" brochure, Dec. 20, 1985.

Primary Examiner—David L. Lacey
Assistant Examiner—Jan M. Ludlow
Attorney, Agent, or Firm—Chester Cekala; William L. Baker

[57] ABSTRACT

The present invention relates to a multiwell apparatus for biological and biochemical analysis which provides for separate collection of filtrate from each well, without cross-contamination therebetween. The present invention provides a manifold plate having an array of filtering wells, each of the wells being closed at its bottom by a planar bottom member providing a filter support surface. A discharge nozzle of passageway depends from each well bottom (planar bottom member) in a direction normal thereto, with one such discharge nozzle or port being provided in fluid communication with each filtering well. Each of these filtrate nozzles or drain ports extends from the lower surface of the planar bottom member to such an extent that it will enter into the well of a conventional multiwell, e.g., microtiter, plate in alignment therewith and mate with the sidewall of the aligned well of the multiwell plate. In this manner, the filtrate can be delivered to the collection well of the multiwell plate as a steady stream, in the manner one would use a pipette, rather than dropwise. The ability to quantitatively collect filtrate into a receiving multiwell plate provides options for improved immunoassays, nucleic acid probe assays and other test procedures.

13 Claims, 8 Drawing Sheets

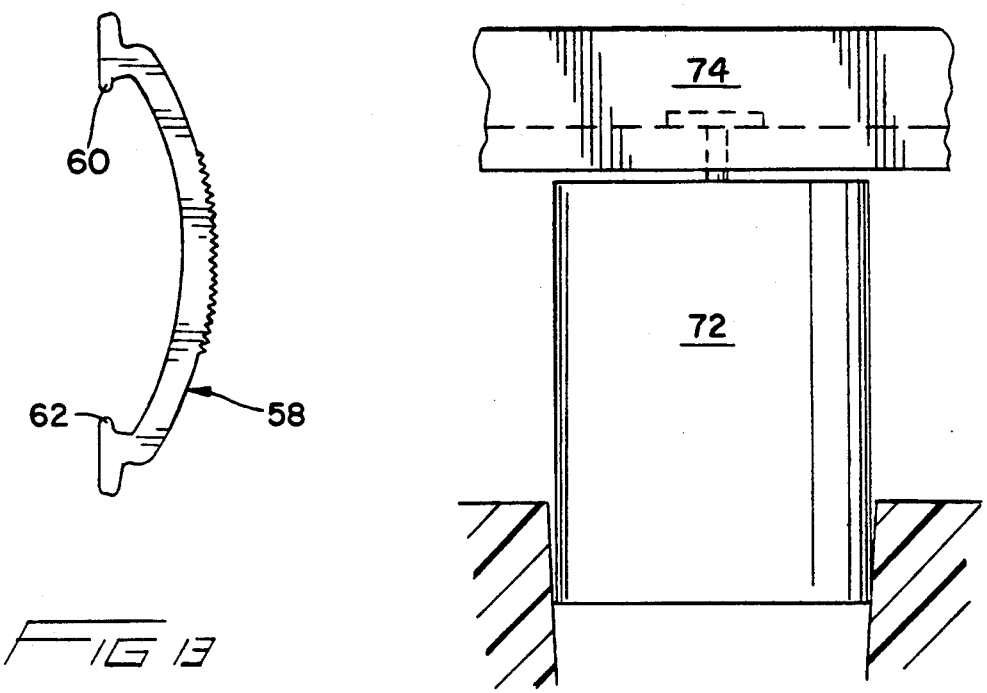
FIG 13
FIG 14
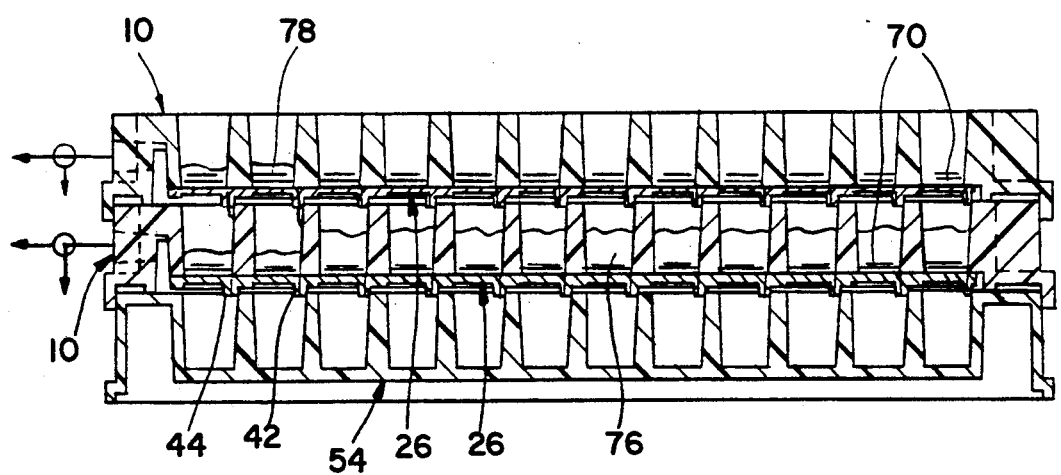
FIG 15

MICROFILTRATION APPARATUS WITH RADIALLY SPACED NOZZLES

BACKGROUND OF THE INVENTION

This invention relates to multiwell apparatus for biological and biochemical analyses.

Microwell test plates, inclusive of the so-called microtiter test plates, have been adapted for a wide range of biological and biochemical laboratory procedures. Most of such apparatus currently in use has been standardized to enable use in conjunction with a standard 96 well microtiter plate having a 12 by 8 array of microwells.

Multiwell trays characterized as "microfiltration trays" are disclosed by U.S. Pat. No. 3,319,792 issued to Leder et al, U.S. Pat. No. 3,730,352 issued to Cohen et al, U.S. Pat. No. 3,888,770 issued to Avital et al, U.S. Pat. No. 3,963,615 issued to Plakas, U.S. Pat. No. 4,167,875 issued to Meakin, U.S. Pat. No. 4,317,726 issued to Shepel, U.S. Pat. No. 4,427,415 issued to Cleveland, U.S. Pat. No. 4,526,690 issued to Kiovsky et al and UK 1,490,362. Similar plates, specifically intended for cell culture are disclosed by U.S. Pat. No. 4,304,865 issued to O'Brien et al, U.S. Pat. No. 4,483,925 issued to Noack and PCT publication WO86/07606. Seiler-et al - U.S. Pat. No. 4,079,009 and Kremer - U.S. Pat. No. 3,928,203 disclose similar microwell plates adapted for use in microchromatography. Likewise, numerous different designs for microwell plates intended for use in immunodiffusion techniques have been patented, e.g. Saravis - U.S. Pat. No. 3,378,347 and Goldsmith - U.S. Pat. No. 3,390,962. U.S. Pat. No. 4,090,850 issued to Chen et al and U.S. Pat. No. 4,246,339 issued to Cole et al disclose multiwell plates specifically designed for immunoassays. All such apparatus disclosed by the prior art includes at least one plate member having an array of wells closed at the bottom with a porous or microporous filter member or membrane. The terminology "microfiltration apparatus" and "multiwell filtration plate" as used herein is intended to embrace all such types of apparatus, regardless of the nature of the permeable medium at the bottom of the individual test wells.

Only a few of the prior art designs for microfiltration apparatus provide for separate collection of the filtrate emanating from the individual wells. With most of the prior art apparatus, attempts to separately collect the filtrate from each well would be unsuccessful or suffer from unreliable results due to cross-contamination between the wells by wicking, capillary action, spilling, running, etc. Further, with many of the prior art designs the apparatus must be used with a separate capital vacuum manifold which is expensive and represents a considerable investment. This is particularly limiting in applications such as genetic research where it is desirable to use numerous microfiltration plates simultaneously. Also, the use of a separate capital manifold limits the ability to stack more than one microfiltration plate in applications requiring serial passage of fluid through more than one plate. An additional problem with much of the prior art microwell apparatus is that little or no provision is made for sanitary handling of the residual materials at the completion of the test. This is a particularly acute problem in assays of bodily fluids containing potentially contagious viral strains and in the case of radiography test procedures where it becomes necessary to handle residual materials and apparatus contaminated by radioactivity.

SUMMARY OF THE INVENTION

Accordingly, it is an object of the present invention to provide a multiwell filtration apparatus which can be adapted for use in any or all of the aforementioned techniques, particularly immunoassays, nucleic acid probe assays, radiography assays, microchromatography and microculture of cell suspensions and tissue.

It is another object of the present invention to provide such an apparatus which is "disposable."

Yet another object of the present invention is to provide a multiwell microfiltration apparatus having its own self-contained vacuum manifold, thus dispensing with the need for capital investment in a separate piece of vacuum manifold apparatus and allowing stacking or serial use of multiple multiwell filtration plates.

Yet another object of the present invention is to provide an microfiltration multiwell plate with provision for separate collection of the filtrate from each test well into respective wells of a conventional microtiter or other plate.

Still another object of the present invention is to provide a novel method for the sanitary handling of filter media or membrane containing or holding a residue resulting from the test procedure.

Still another object of the present invention is to provide such an apparatus having the capability for a quantitative recovery of liquid medium from each test well.

Yet another object of the present invention is to provide such an apparatus and method particularly adapted for radiography techniques.

Still another object of the present invention is to provide such an apparatus and method particularly adapted for microchromatography.

Yet another object of the present invention is to provide such an apparatus and method particularly adapted for the microculture of cell suspensions and/or tissue.

These and other objects and features of the invention will become apparent to those skilled in the art from a reading of the detailed description to follow, in conjunction with the drawings and appended claims.

In order to provide for separate collection of filtrate from each well of an array of test wells, without cross contamination therebetween, the present invention provides a manifold plate having an array of filtering wells, each of the wells being closed at its bottom by a planar bottom member providing a filter support surface. A discharge nozzle or passageway depends from each well bottom (planar bottom member) in a direction normal thereto, with one such discharge nozzle or port being provided in fluid communication with each filtering well. Each of these filtrate nozzles or drain ports extends from the lower surface of the planar bottom member to such an extent that it will enter into the well of a conventional multiwell, e.g. microtiter, plate in alignment therewith and mate with the sidewall of the aligned well of the multiwell plate. In this manner, the filtrate can be delivered to the collection well of the multiwell plate as a steady stream, in the manner one would use a pipette, rather than dropwise. The ability to quantitatively collect filtrate into a receiving multiwell plate provides options for improved immunoassays, nucleic acid probe assays and other test procedures.

In one embodiment the planar bottom members are integral with the manifold plate, the whole being molded as a single piece. In a second embodiment a separately formed filter support plate closes the bottoms of the test wells, thus providing a planar bottom member for each filtering well, the filter support plate being sealed to the manifold plate around the bottom of each filtering well.

In a preferred embodiment, the aforementioned microfiltration apparatus has the filtrate discharge nozzle or port provided in a skirt which is adapted to mate with the interior cylindrical surface of a well of a conventional microtiter plate. In the preferred embodiment the skirt is a segmented skirt, i.e. it is in the form of two pair of diametrically opposed pins, with one of the four pins serving as the filtrate discharge nozzle for a given filtering well.

In another of its aspects, the apparatus of the present invention has novel features which enable a uniquely different approach to the handling of contaminated filter media. Toward this end, the aforementioned skirt is adapted to function as an alignment guide in conjunction with a punch. Thus the skirt, preferably segmented to avoid airlock, circumscribes an area aligned with the axis of a given well in the manifold plate, which circumscribed area is equal in diameter to or slightly smaller than the bottom of the well. The skirt is tapered inwardly toward its axis to receive and guide a punch into axial alignment with the filtering well. Thus, after completion of filtration, the plate may be inverted and a punch is received in the skirt and driven through the bottom of the planar bottom member and the filter medium disposed thereon. The cut bottom of the planar bottom member thus serves as a sanitary punch, shearing the filter medium, with the well itself functioning as a cutting die. The blanks cut from the well bottoms and corresponding blanks cut from the filter medium may be received onto a radiography film or into any collection device appropriate to the particular test procedure for which the apparatus is used. Preferably, each punch is one of a linear array of eight punches which are used in sequence along a given row of eight filtering wells. After the last well of a given row has been punched through, the linear array of punches is moved forward to the next row and the process is repeated, without risk of contamination or carryover by the punches.

In another of its aspects, the present invention provides a disposable microfiltration assembly which includes its own disposable vacuum manifold. Toward this end, a manifold plate is provided with parallel, spaced inner and outer peripheral skirts depending from its upper planar surface. The outermost skirt serves to align the apparatus with and mate with a conventional multiwell plate. Preferably, this outer- most skirt is of such a length that when the manifold plate assembly is placed on a planar surface, no well bottom or filtrate discharge nozzle will touch that planar surface. In other words, the manifold plate assembly of the present invention may be placed on top of a laboratory bench without fear of contamination. The innermost skirt is designed to engage and seal with the upper planar surface of a collection plate, which may be either a conventional microtiter plate, another manifold plate, or an open tray for receiving wash fluids. In order to seal the innermost skirt to the collection plate, the free end of the innermost skirt may be provided with a downwardly opening peripheral channel and an elastomeric gasket contained therein or a separately molded elastomeric gasket may be inserted between the innermost and outermost skirt, which gasket has an inner beaded lip which extends under the innermost skirt. The length of this innermost skirt is such as to maintain a small clearance between the bottom surface of the filter support plate and the top planar surface of the collection plate and vacuum communication between this clearance space and the interior of the manifold plate may be provided in any suitable manner, for example by provision of apertures extending through the filter support plate. A vacuum port is provided which extends laterally through both skirts into the interior of the manifold plate. Thus, a conventional petcock or a fitting associated therewith may be inserted into the vacuum port and the space surrounding the exteriors of the filtering wells can be thereby evacuated to draw filtrate through the filter discharge nozzles.

The present invention also provides for several novel handlings of otherwise conventional radiography techniques. For example, a manifold plate may be placed on top of x-ray film in a black box or cassette after the test reagents have been added to the respective filtering wells, whereby the x-ray film is developed. In another radiography method in accordance with the present invention, the filtered residue to be analyzed by radiography is collected in the well bottoms of a manifold plate in accordance with the present invention and then that assembly is inverted and an area of the bottom of each well is punched through onto an x-ray film placed below same in a dark room or dark box whereby the filter medium with radioactive residue to be analyzed comes into direct contact with the x-ray film.

The present invention also provides a novel cell culturing method employing the apparatus described above. The cells are cultured in the wells of one manifold plate (culture plate), with a second manifold plate, as described above, mounted on top of the culture plate with the array of filtering wells of the top manifold plate aligned with the wells of the culture plate and separated therefrom by a semipermeable membrane in the bottom of each filtering well of the top manifold plate. Nutrient solution added to the uppermost filtering well array is "sterilized" by passage through the semipermeable membrane. Each well in the culture plate is fed nutrient containing solution through the semipermeable membrane and through a filtrate discharge nozzle as described above. When desired, culture medium is similarly harvested from the culture plate containing the growing cells by placing the culture plate, with the manifold plate on top of it, on top of a collection plate and applying a vacuum to the port of the culture plate.

BRIEF DESCRIPTION OF THE DRAWINGS

In the drawings:

FIG. 13 is a side elevational view of a "C"-clip depicted in FIG. 12;

FIG. 14 is a perspective view of a punch as used in the present invention;

FIG. 15 is a side elevational view, in cross-section, of an assembly for culturing cell suspensions or tissues in accordance with the present invention;

DESCRIPTION OF THE PREFERRED EMBODIMENTS

FIGS. 1-10 illustrate embodiments of the present invention wherein a single filter support plate 26 forms the bottoms of all wells of a manifold plate 10.

Figure 1:
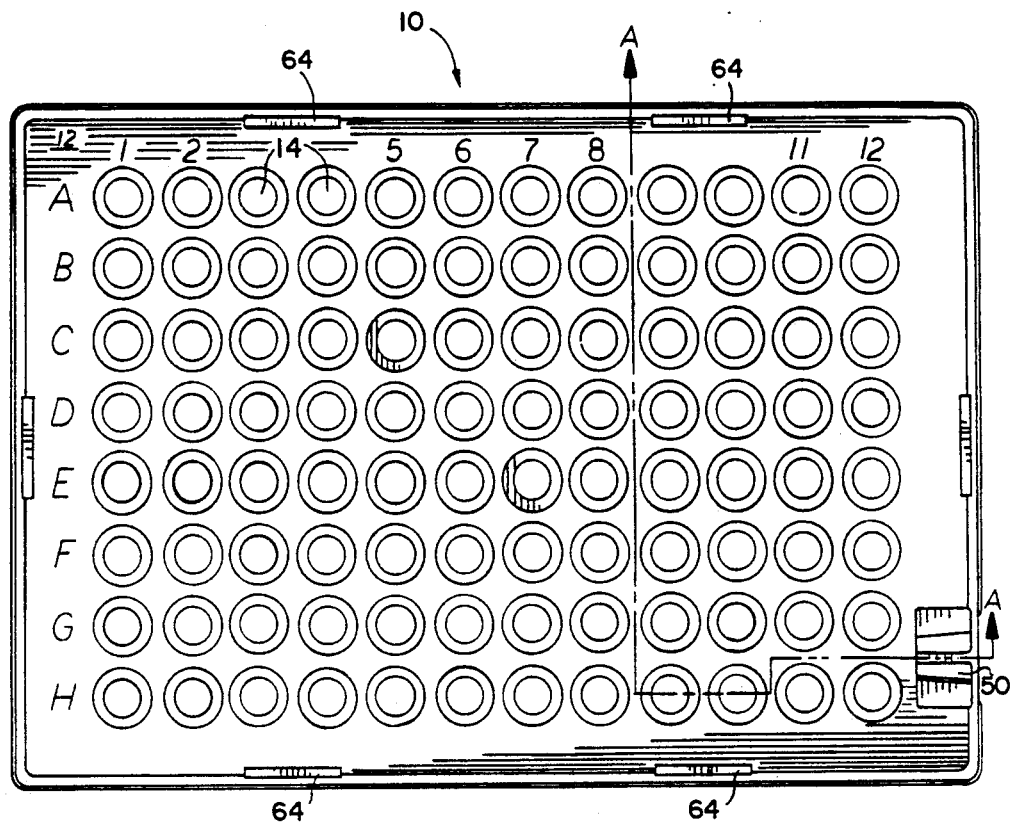
FIG. 1 is a top plan view of one embodiment of a manifold plate of the microfiltration apparatus of the invention.
Figure 2:
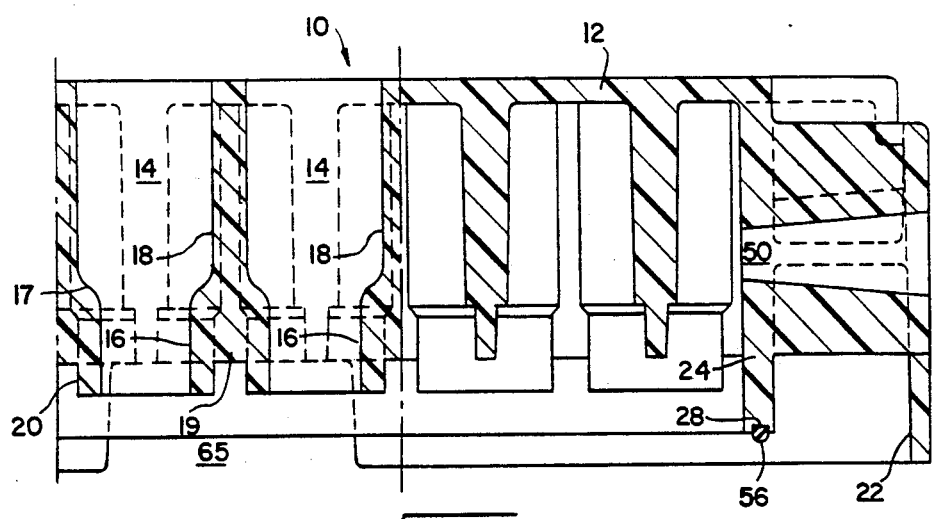
FIG. 2 is a right side elevational view of the manifold plate of FIG. 1, in cross-section, taken along A—A in FIG. 1.

FIGS. 1 and 2 show a manifold plate 10 which constitutes one element of a complete embodiment of the microfiltration apparatus of the present invention. As is illustrated in FIG. 1, the manifold plate 10 has an upper planar surface 12 and an array of wells 14 depending therefrom. The array in the illustrated embodiment consists of 96 wells in an 8 horizontal row (A-H) and 12 vertical row (1-12) arrangement. Such a 96 well array has become a standard in the industry for microtiter plates in general. As seen in the cross-sectional view of FIG. 2, each well 14 is formed with a bore 16 and a counterbore 18. The transition between bore 16 and counterbore 18 is preferably a smooth "S"-shaped surface 17. Each well 14 terminates in a male fitting 20 which is received in a mating depression 32 in the upper surface of a filter support plate 26 (see FIG. 6) as described below.

Figure 3:
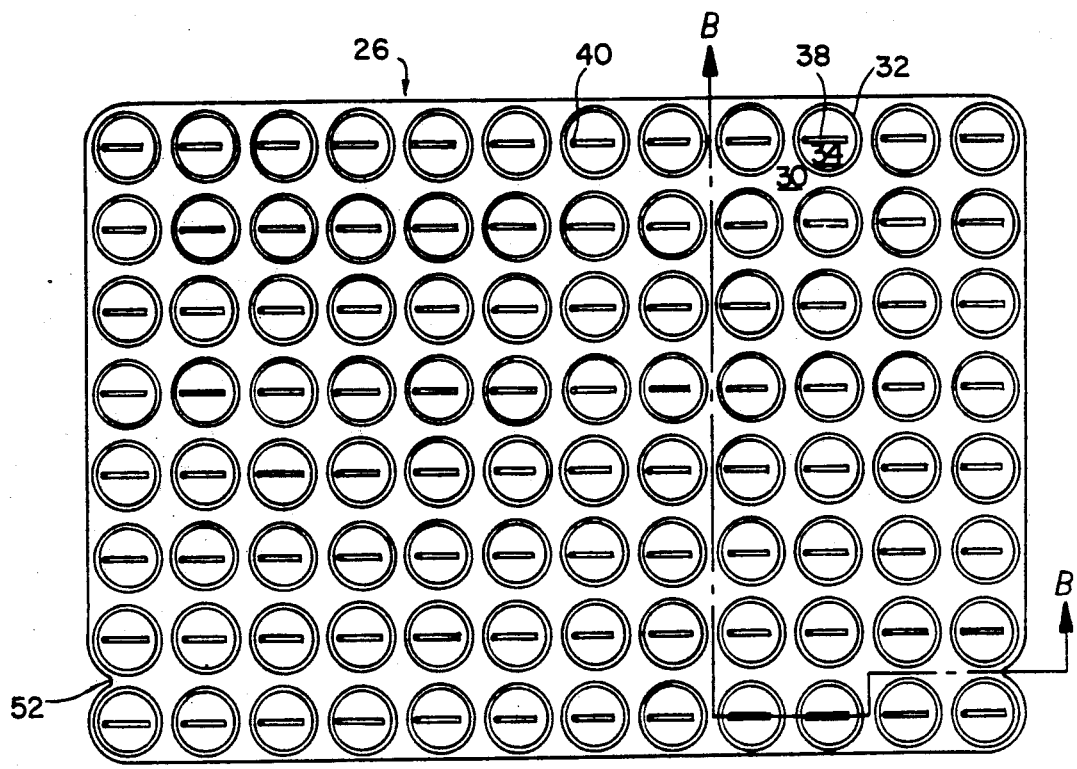
FIG. 3 is a top plan view of a filter support plate which mates with the bottom of the manifold plate of FIGS. 1 and 2.
Figure 4:
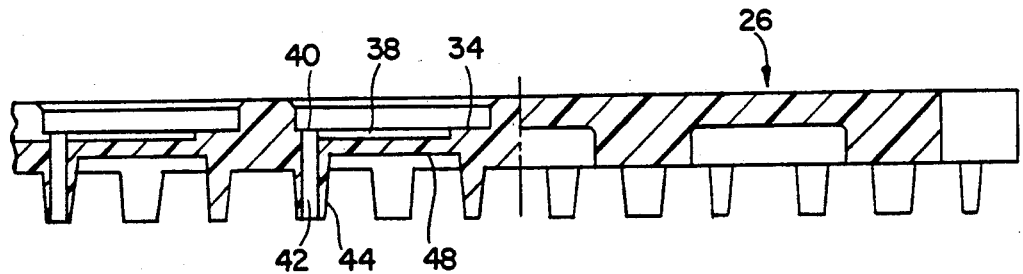
FIG. 4 is a right side elevational view, in cross section along B—B in FIG. 3.
Figure 5:
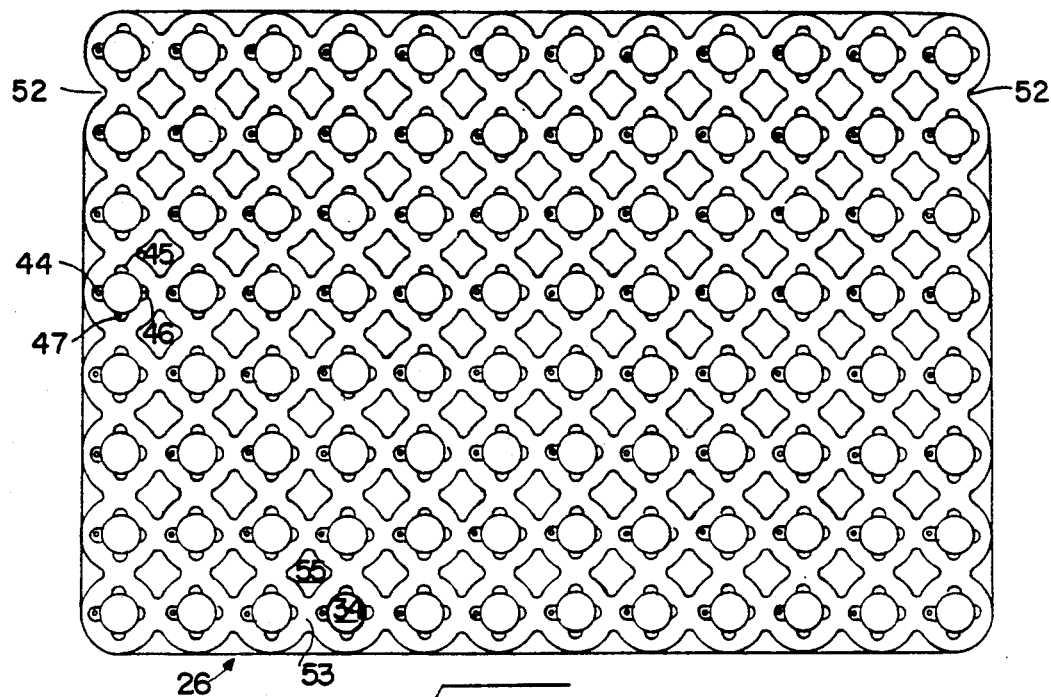
FIG. 5 is a bottom plan view of the filter support plate depicted in FIGS. 3 and 4.
Figure 6:
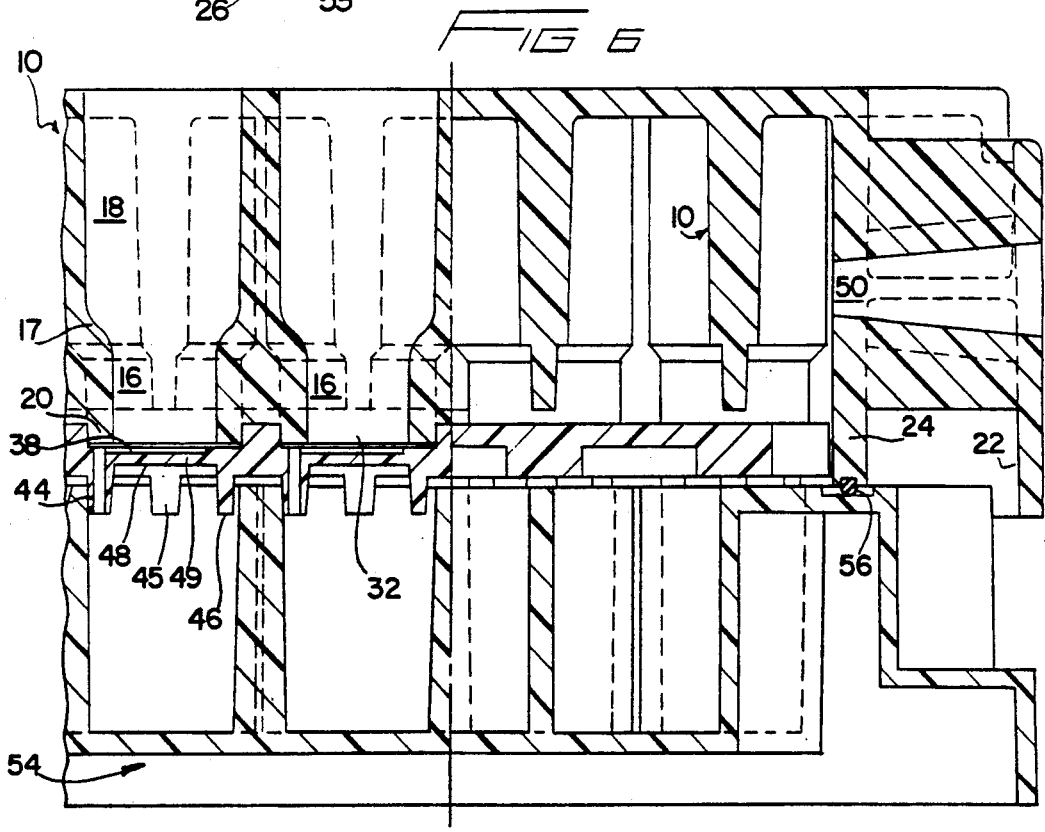
FIG. 6 is a partial side elevational view, in cross section, showing the manifold plate as depicted in FIG. 2 and the filter support plate as depicted in FIG. 4 assembled together with a conventional filter medium and a conventional microtiter plate.

A second element of this first-described embodiment of the present invention, the filter support plate 26, is illustrated in FIGS. 3-5. As seen in FIG. 3, the filter support plate 26 has a top planar surface 30 having a plurality of depressions 32 equal in number to and alignable with wells 14. The sidewall of each depression 32 is slightly tapered and is of such a size as to mate with male fittings 20 of the manifold plate 10 as shown in FIG. 6. Thus, the manifold plate 10 and the filter support plate 26 are assembled by aligning the two together with a male fitting 20 above each depression 32. A circumferential weld between the mating surfaces of depression 32 and male fitting 20 is formed for each well 14 in a conventional manner, for example by shear joint ultrasonic welding. These welds, extending around the circumference of the bottom of each well 14 are also hermetic.

Thus, the bottom 34 of each depression 32 closes the bottom of a well 14. A circular piece of filter medium is placed in the bottom of each well 14 flush against surface 34. As is further shown in FIG. 3 each well bottom (filter support surface) 34 has a channel 38 extending across its surface to collect filtrate passing through the filter medium. The filtrate passes through channel 38 and into an aperature 40. As seen in FIG. 4, 40 opens into a filtrate discharge passage 42 which extends through pin member 44. Pin 44 is one of four pins, shown as 44, 45, 46 and 47, symmetrically arranged around an axis alignable with a well 14. These pins 44, 45, 46 and 47 together form what is referred to herein as a segmented skirt. The spacing of these pins 44, 45, 46 and 47 is such that they mate with the inside surface of a well of a microtiter plate (or another manifold plate) and thereby assist in establishing and maintaining alignment. The gaps between the pins allow air to escape from the filtrate collection wells in the microtiter plate and thus prevent airlock and the potential for cross-contamination between wells by capillary action, etc. In embodiments not employing the punch feature, described in detail below, only a single pin, i.e. that provided with a filtrate discharge nozzle 42 is necessary. However, in embodiments employing the punch feature at least two and preferably at least three pins are provided.

As is further seen in FIGS. 4 and 5 the pins 44, 45, 46 and 47 circumscribe an area 48 which is coaxial with the depression 32. It can also be seen that 48 itself is indented from the lower planar surface of the filter support plate 26 so that the filter support plate between surfaces 34 and 48 is substantially thinner than the thickness of the plate elsewhere. This thinness of the filter support plate at the bottom of each well 14 plays an important part in the utilization of the apparatus of the present invention as will be explained below. The diamond shaped areas 55 (FIG. 5) are substantially thinner than surrounding areas 53.

The location of these pins relative to the axis of the area circumscribed thereby (the wall axis) i.e. the radial distance between a given pin and that axis, is important because it is designed to have each pin contact the inner cylindrical wall of a well of a microtiter plate placed in alignment therewith. As noted above, such an arrangement assists in alignment of the filter support plate with a microtiter plate (or another manifold plate). It also provides for a quantitative transfer of liquid volume from a test well 14 to a collection well of a microtiter plate. In accordance with the present invention the pin 44 which carries the filtrate passage 42 engages the sidewall of a collection well so that the filtrate emanates from pin 44 as a steady stream, rather than drop by drop. The tip of pin 44 extends below the lip of the collection well, e.g. suitably 1-2 mm below the lip. Thus, pin 44 functions in the manner a properly used pipette would function to deliver liquid. In other words, instead of a drop adhering to the tip of a nozzle centered within the well, in accordance with the present invention, the liquid which would otherwise form such an adhering drop flows smoothly down the sidewall of a collection well and a maximum volumetric transfer of liquid from each well 14 into a collection well is thereby attained. The area 48 circumscribed by the pins is coaxial with and substantially equal in diameter to the bore 16.

As seen in FIGS. 2 and 6, the manifold plate 10 has an outer peripheral skirt 22 which performs two distinct functions. Firstly, the outer skirt 22 serves to align the manifold plate 10 (and filter support plate 26) with a conventional microtiter plate (or second manifold plate) and secures the microtiter plate (or second manifold plate) in alignment therewith. Secondly, skirt 22 is of such a length that with the filter support plate 26 in place, the manifold plate 10 may be placed on a laboratory bench or on any planar surface without any portion of the filter support plate contacting that surface. Thus, the microfiltration apparatus of the present invention may be handled rather freely within a lab without fear of contamination by whatever might be present on the counter or benchtop constituting the work station.

Spaced inboard from the outer peripheral skirt 22 is a second or inner peripheral skirt 24 which is shorter than skirt 22. Skirt 24 also serves two purposes. Firstly, it is of such a length that there will be a suitable clearance between the lower surface of the filter support plate 26 and the top surface of a microtiter plate or other collection tray to allow for a vacuum to be established within the microtiter plate for the purpose of drawing filtrate through the filter support plate by vacuum. As can be seen in FIG. 6, the filter support plate 26 is of such a size that it can be fit within the inner skirt 24. In fitting together the manifold plate 10 and the filter support plate 26, the terminus of each well 14, i.e. male fitting 20, is received in a mating depression 32 in the upper surface of the filter support plate 26. Each male fitting 20 is then ultrasonically welded to the filter support plate 26 thereby forming a seal at the bottom of each well 14 surrounding the filter medium. With the filter support plate 26 in place, the inner skirt 24 extends below same a sufficient distance to provide the aforementioned clearance, suitably about 1 mm. Secondly, the inner skirt 24 provides a continuous hermetic seal around the periphery of the top surface of a collection plate. Thus, the inner skirt 24 has downwardly opening channel 28 in which is carried a bead of a suitable gasket material, e.g. a silicone elastomer 56.

Figure 7:
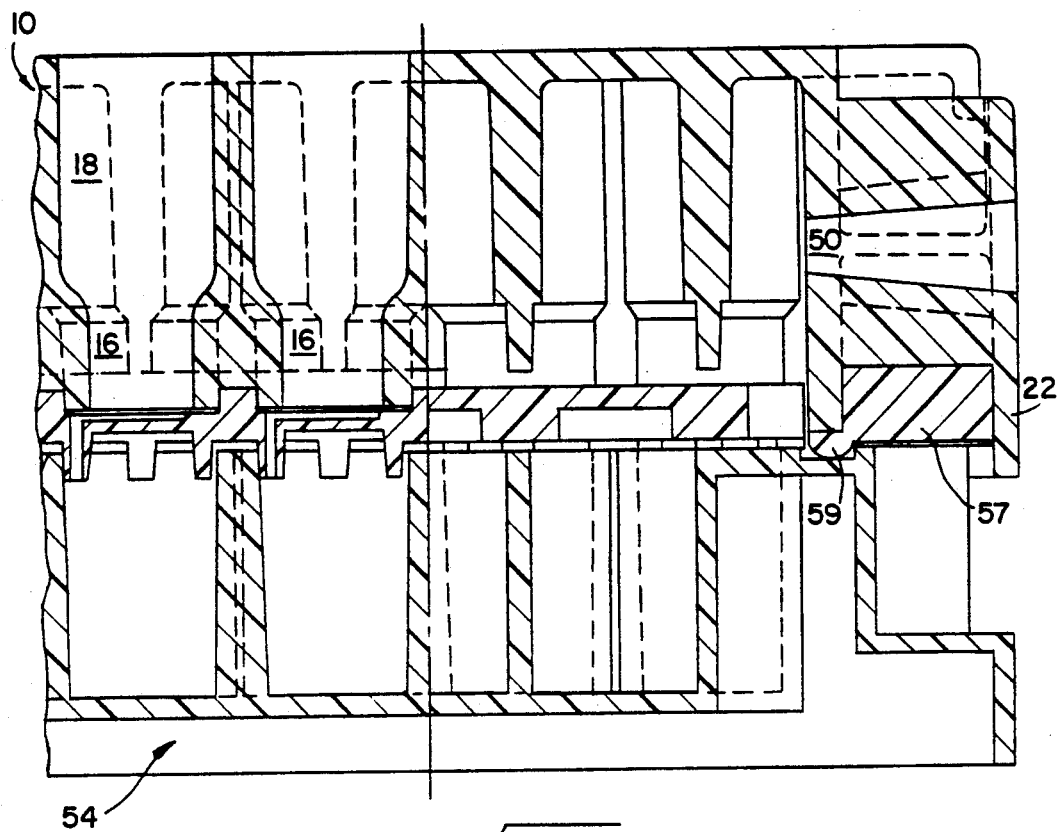
FIG. 7 is a view similar to that of FIG. 6 but showing an alternative embodiment for a seal between a manifold plate and a collection plate or a second manifold plate.

In an alternative embodiment, as shown in FIG. 7 and now considered an improvement over that just described, a gasket 57 provides the seal between the manifold plate 10 and a microtiter plate 54 (or another manifold plate 10). The gasket 57 has a lip 59 which fits under the end of the inner skirt 24.

For the purpose of evacuating the space underneath the filter support plate the apparatus of the present invention is provided with a vacuum port 50 which extends through skirts 22 and 24 as shown in FIG. 2. The area beneath the filter support plate 26 is also evacuated through port 50 by provision of a number of openings between the edge of the filter plate 26 and the inner skirt 24 of the manifold plate 10. In other words, as shown in FIGS. 3 and 5, the filter support plate is provided with several notches 52 at its periphery. A luer taper petcock (not shown) or any other suitable vacuum fitting may be press fit or threaded into the vacuum port 50 to provide the necessary connection. Thus, the apparatus of the present invention provides its own vacuum manifold and dispenses with the need for investment in the rather expensive conventional vacuum manifolds heretofore used in connection with the prior art microfiltration apparatus.

Figure 12:
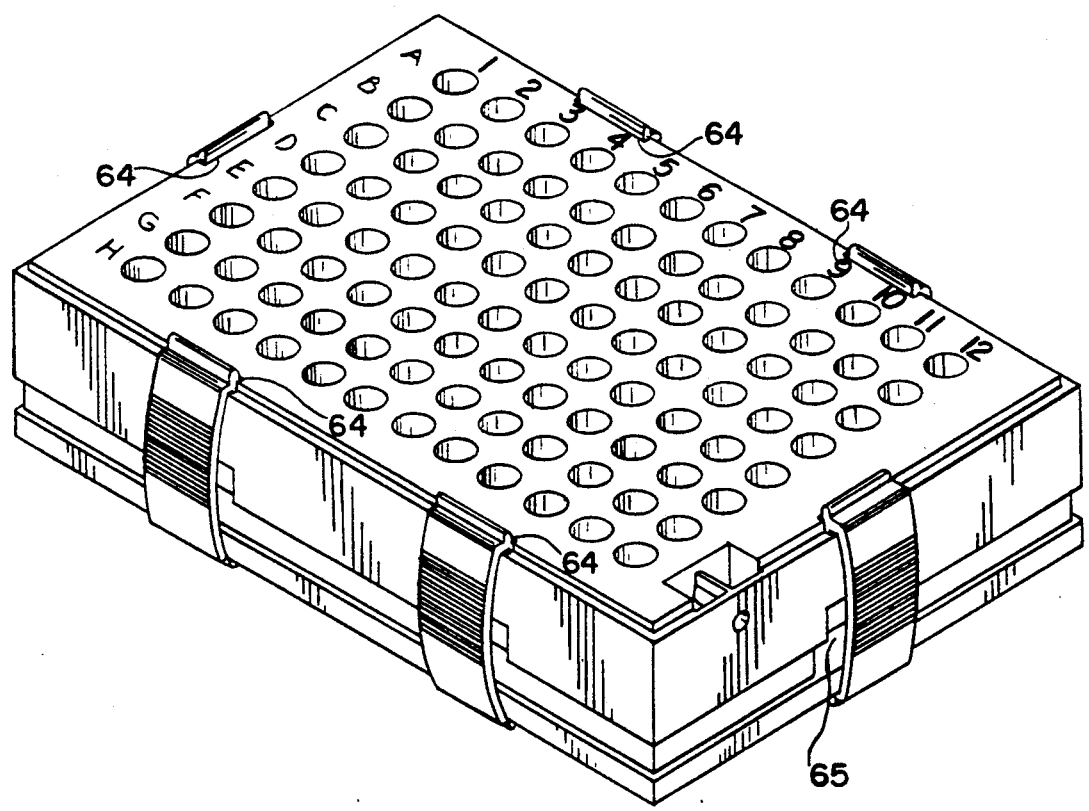
FIG. 12 is a perspective view of the manifold plate of FIGS. 1 and 2 and the filter plate of FIGS. 3-6 clipped together with a conventional microtiter plate.

As shown in FIG. 6, the manifold plate 10 with the filter support plate 26 attached within inner skirt 24, is designed to align with and mate with a conventional microtiter plate indicated at 54 in FIG. 6. Thus, each of the 96 wells of the manifold plate will be coaxial with one of the 96 wells of a conventional titer plate. As noted above, a hermetic seal between the top planar surface of the microtiter plate 54 and the lower end of skirt 24 is provided by a bead of gasket material, e.g. a silicone elastomer 56, molded to attach in a downwardly opening channel 28, as shown in FIG. 6, or a gasket 57 as shown in FIG. 7. As is shown in FIG. 12, the whole assembly may be optionally held together with a number of C-clips 58, one of which is shown in more detail in FIG. 13. Protrusions 60 and 62 of C-clip 58 are received, respectively, in a cutout or indented groove 64 provided at the periphery of the manifold plate 10 and the bottom skirt of a microtiter plate, or a cutout 65 in the bottom of another manifold plate.

Figure 10:
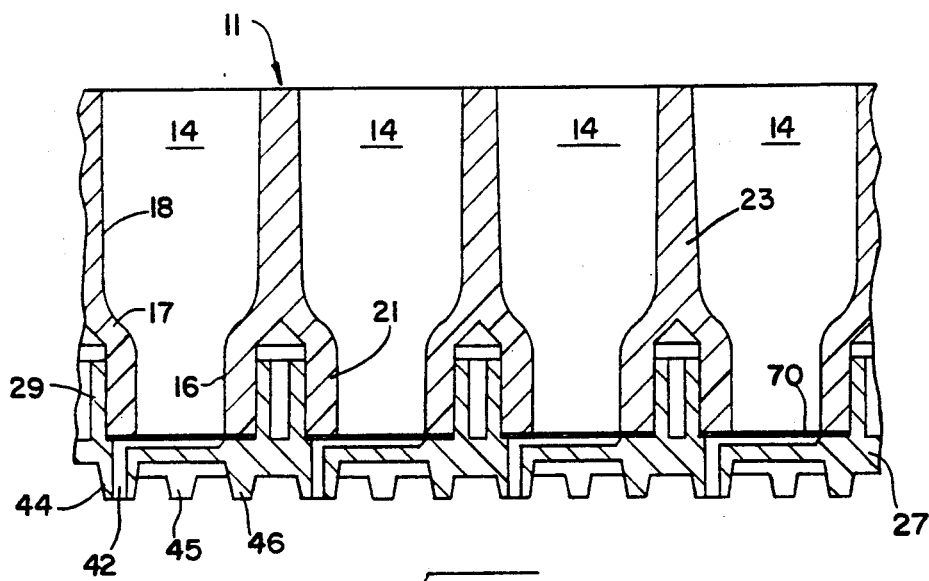
FIG. 10 is a view similar to that of FIG. 6 but showing an alternative embodiment wherein the manifold plate and filter support plate have been modified to provide a press fit therebetween.

FIG. 10 depicts an alternative embodiment which, at the present point in time, is the most preferred embodiment. As shown in FIG. 10 the manifold plate 11 has annular male members 21 which are substantially the same length as members 20 in the previously described embodiments but the webs 23 connecting same extend downward from the planar surface 12 only as far as the terminus of counterbore 18. Otherwise, manifold plate 11 in the embodiment of FIG. 10 is similar to manifold plate 10 of the previously described embodiments. Likewise, the filter support plate 27 is similar to the filter support plate 26, except that instead of depressions 32, the filter support plate 27 carries an array of annular members 29, each of which mates with a male member 21 to provide a press fit heremetic seal therebetween. Another difference in the filter support plate 27 is that indented areas ("diamonds") 55 have been omitted so that the entire area surrounding the annuli 29 is of uniform thickness. Because no web extends between the press fit areas, the annular members 29 may swell due to the pressure of the press fit without causing warpage of the manifold plate.

Figure 11:
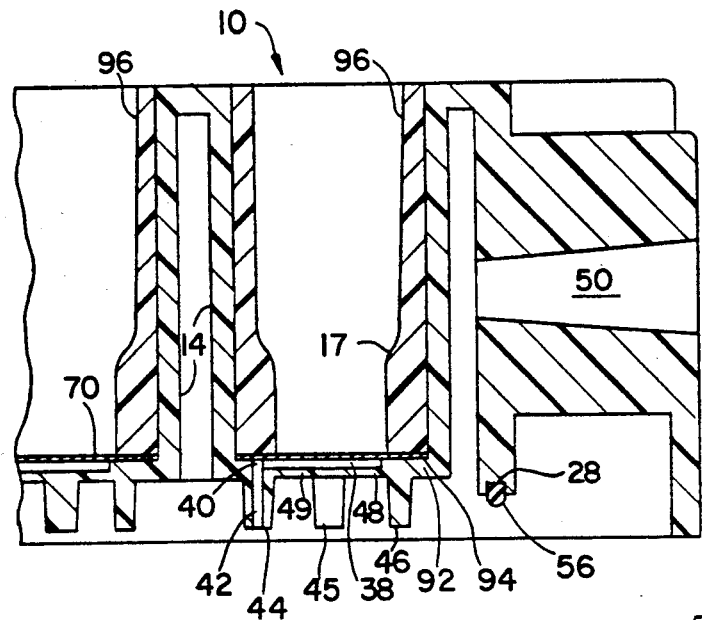
FIG. 11 is a perspective view of an alternative embodiment wherein the filter support surfaces and well bottoms are integrally molded with the manifold plate as a single piece.

Another embodiment of the present invention is illustrated in FIG. 11 wherein elements identical to those of the embodiments of FIGS. 1-9 are indicated by the same reference numerals. Instead of a filter support plate, planar bottom members 92 are provided for each well 14 and are formed integrally therewith as a single molded piece. The bottom members 92 each present a filter support surface 94 having a filtrate collection channel 38 as in the previously-described embodiment. A disc of filter medium 70 is placed in the bottom of each well 14 against filter support surface 94 and is sealed in place around its periphery by press-fitting an annular member 96 within the well 14. It should be noted that the annular member 96 provides an inner well geometry identical to that of the first-described embodiment, inclusive of the "S"-shaped shoulder 17.

Figure 8:
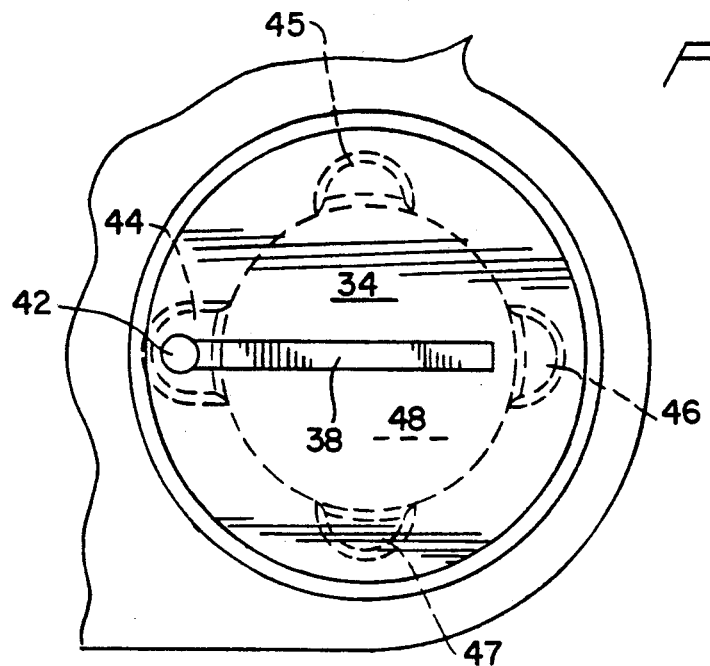
FIG. 8 is a top plan view of one well of the filter support plate of FIG. 3.

In embodiments where the filter support plate 26 and the manifold plate 10 are separately formed and then welded together, a single sheet of membrane filter, of dimensions approximating those of the filter support plate, may be laid on top of the filter support plate 26 and then the whole is press-fit against the bottom of manifold plate 10. In such an embodiment, as depicted in FIG. 8, as the male fitting member 20 is forced into the depression 32, it cuts a circular piece of filter 70 out of the sheet and forces it to the bottom of the depression 32. In other words, male member 20 serves as a punch and the depression 32 serves as a die for cutting the filter. In contrast, in the single piece construction shown in FIG. 11, discs of filter medium 70 must be placed into each well 14 by punching or other means. Of course, in the two piece constructions of FIGS. 1-10 it is also possible to use separately formed disks of filter medium 70.

The nature of the filter medium 70 will vary widely depending upon the end use for which the microfiltration apparatus in intended. For example, for microchromatography applications the filter medium 70 may be a 20 micron fibrous paper of paper pulp, glass, cellulose acetate, or a mixture thereof. For cell culturing a hydrophilic microporous membrane having a pore size of 0.5-1 micron, preferably 0.6 microns, is preferred. For biological binding assays any affinity reactive membrane, e.g. nitrocellulose, may be used.

Figure 9:
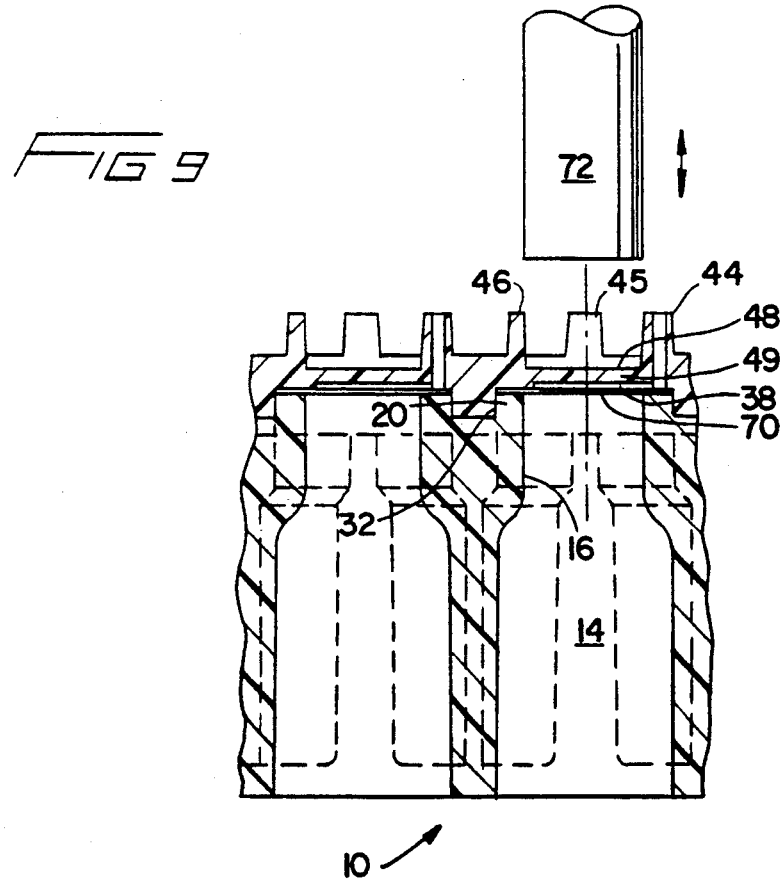
FIG. 9 is a partial side elevational view of the manifold plate and filter support plate of FIG. 6 inverted to receive a punch.

FIG. 9 shows the manifold plate 14 and filter support plate 26 inverted for receiving a punch 72. The punch 72 is of a diameter approximately equal to that of circumscribed area 48 and bore 16. It can be seen that punch 72 will mate with pins 44, 45, and 46 (and 47, not shown) which serve as a guide for receiving and guiding punch 72. As punch 72 passes through filter plate 26 it will push, ahead of it, a cut out portion 49 which will serve as the cutting punch, shearing the filter, and as a piston to wipe the walls of bore 16 thereby cleaning off any residue thereon. The bore 16 serves as a die working together with the punch to shear the support plate and filter. The punched portion of the filter medium 70, with whatever has been deposited thereon or bound thereto during the course of the assay, is pushed down out of bore 16, leaving behind an annular piece of filter medium pressed beneath male member 20 in the first embodiment and beneath annular member 96 in the second embodiment. If the well 14 is formed of a single, constant diameter, i.e. without a shoulder 17, bore, the cut-out portion of the filter plate 29 will wipe a substantial length of the well.

FIG. 14 shows one punch 72 of a linear array of eight punches mounted within a punch holder 74 which allows the punches 72 to move slightly within a horizontal plane to properly align themselves with the axis of a well 14. The punches 72 are aligned with a horizontal row of eight wells 14 and operated in sequence to punch out areas 49 one at a time and then stepped to the next horizontal row of wells where the punching operation is repeated.

An example of an immunoassay that can be performed using the apparatus of the present invention is a sandwich EIA. The apparatus for performing the immunoassay would include: (1) a manifold plate having an upper planar surface and an array of filtering wells for receiving liquid samples to be filtered, each of the wells being closed at its bottom by a planar member providing a filter support surface for a filter medium; inner and outer skirts depending from the upper planar surface and surrounding the array of filtering wells, the outer skirt being adapted to mate with the exterior sidewalls of a collection plate, and the inner skirt terminating at a lower rim and being sufficiently long to maintain a fixed space between the well bottoms and a planar surface of a collection plate engaged by the lower rim; sealing means for forming a hermetic seal between the lower rim of the inner skirt and the top of the collection plate; the inner skirt defining an interior space within the manifold plate; a drain port, associated with the bottom of each of the filtering well bottoms, for draining filtrate from the associated well; and a vacuum port for evacuating the interior and fixed spaces thereby drawing filtrate through the drain ports; (2) a filter medium disposed in the bottom of each of the filtering wells of the manifold plate; (3) a waste receiving tray sized to engage and seal hermetically to the inner skirt of the manifold plate; and (4) a conventional multiwell microtiter plate suited to optical measurement which will seal hermetically to the inner skirt of the manifold plate.

A primary antibody is adsorbed or covalently immobilized to the filter medium. Alternatively, equal aliquots of a suspension containing microbeads with primary antibody adsorbed or covalently immobilized are added to each of the filtering wells. In order to perform the immunoassay, the manifold plate is placed on top of the waste receiving tray. A sample containing antigen to be assayed is then placed within the filtering wells and the sample is filtered through the filter medium at a controlled rate by applying a vacuum beneath the filter support plate. The antigen of interest is thus captured and the remaining sample is passed into the waste receiving tray. A solution containing an excess of a second antibody conjugated to an enzyme is then added to each filtering well and again filtered through the filter medium at a controlled rate. Several volumes of a wash buffer solution are then filtered through each filtering well to remove any unbound enzyme conjugate. The waste receiving tray is then removed from under the manifold plate and replaced with the conventional multiwell microtiter plate. An excess of colorless enzyme substrate solution is added to each filtering well and again filtered through at a controlled rate by vacuum. Optionally, a volume of wash buffer solution may be filtered through the filtering wells to quantitatively transfer all enzyme product to the microtiter plate. The microtiter plate is then read on a conventional multiwell spectrophotometric plate reader. Thus, a quantitative assay for anitgen is obtained.

CELL CULTURING

FIG. 15 depicts two manifold plate assemblies 10 and 10' in accordance with the present invention combined with a conventional microtiter plate 54 in an arrangement suitable for cell cultivation. Both the upper and the lower manifold plate assemblies 10 and 10' are provided with a filter medium 70 which may be any suitable hydrophilic microporous membrane, e.g. a cellulose ester or nylon membrane. The membrane will typically have a pore size of 0.2-1 micron, preferably 0.6 microns. Cells and cell culture medium 76 are placed into each of the 96 wells of the lower manifold plate assembly 10' for incubation. Nutrient, drugs to be tested or labeled precursor in liquid form 78, may be placed in the wells of the upper manifold plate/filter support plate assembly 10 from time to time for feeding to the cell cultures in the wells of the lower manifold plate 10'. The nutrient liquid may be sterilized as it passes through the microporous membrane 70 in the upper manifold plate 10, if that membrane has a pore size of 0.2 $\mu$ or less. The diameter of the filtrate passage 42 in each pin 44 is such that the pressure of the hydrostatic head of the culture medium in each well of the lower manifold plate is offset by the capillary force within passage 42 and the force of drop adhesion thereto. The result is that there will be transfer of only small volumes of liquid from the cell culture medium in plate 10' into the wells of the microtiter plate 54, until such time as a suitable vacuum is applied to the lower manifold plate 10'. A liquid head corresponding to a volume of 50 μl-100 μl will remain in wells 16 of the lower manifold plate 10 when plates 10 and 10' are vented to atmosphere. If a vacuum is applied only to plate 10, then fluid added to plate 10 will immediately filter into the wells of plate 10' and none of the volume in the wells of plate 10' will filter into plate 54. If a higher vacuum is applied to plate 10' or if plate 10 is vented and vacuum is applied to 10' then all the volume in the wells of plate 10' will transfer to the wells of plate 54.

Thus, the arrangement shown in FIG. 15 dispenses with the absolute need for using a sterile hood during feeding of nutrients to a microculture plate. Further, there is no loss of cells in feeding or harvesting as occurs by supernate aspiration in the prior art methods.

RADIOGRAPHY

Figure 16:
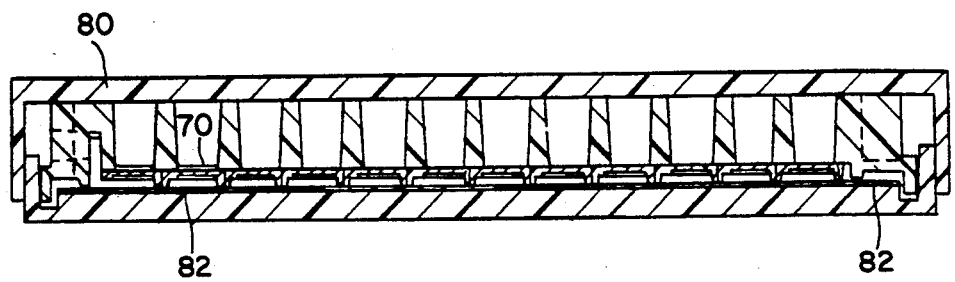
FIG. 16 is a side elevational view of a manifold/filter support plate assembly adapted for radiography in accordance with the present invention.
Figure 17:
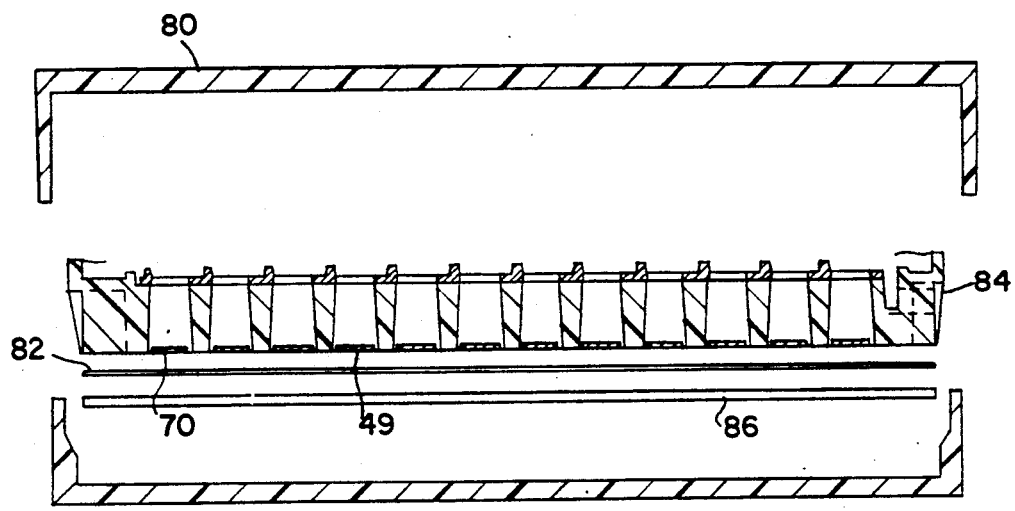
FIG. 17 is a side elevational view of a manifold/filter support plate assembly adapted for another radiography method in accordance with the present invention.

FIGS. 16 and 17 depict two different methods for adapting the present invention for use in radiography. A radiolabeled species is collected on a suitable filter medium in a manifold plate assembly in accordance with the present invention. After removal of the filtrate by vacuum, the manifold plate assembly may be placed in a molded, light impervious, e.g. black, cassette 80 with a suitable film (Kodak "X-OMAT") contained therein as depicted in FIG. 16. The film is thereby exposed to whatever radiolabeled species might be present on or in the filter medium 70. In an alternative embodiment illustrated in FIG. 17, after recovery of the radiolabeled species on the filter medium 70, the manifold plate has its top planar surface covered with a plastic film such a "SARAN" 84 and the whole is then inverted and punched with cut elements 49 being held suspended on the plastic film 84. After punching, the whole may be placed inverted into a light impervious cassette 80 containing a suitable film 82, e.g. Kodak "X-OMAT", backed by an enhancing screen 86 for exposure of the film.

MICROCHROMATOGRAPHY

Figure 18:
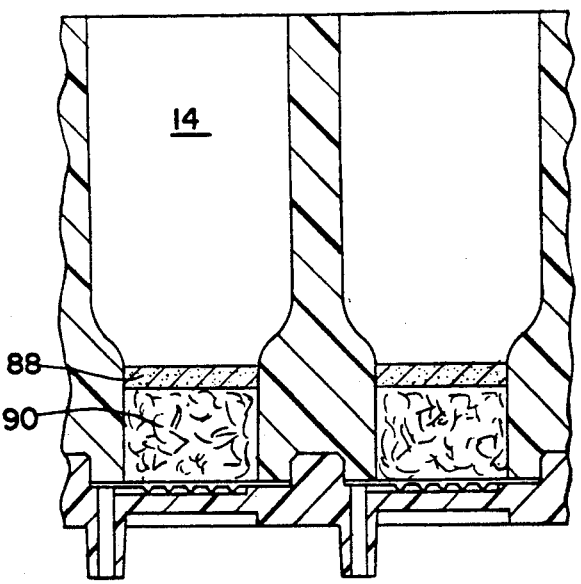
FIG. 18 is a fragmented side elevational view, in cross-section, of a manifold plate/filter plate assembly adapted for a method of microchromatography in accordance with the present invention.

The apparatus of the present invention may be adapted for use in microchromatography techniques by filling wells 14 of a manifold plate 10 with ion exchange, reverse phase or desalting or other media. A sheet of thin "POREX" or other suitable porous media 88 is then placed on a steel die plate with 96 holes equal in diameter either to bore 16 or counterbore 18, aligned with the filtering wells 14, which die plate, in turn, rests on the top planar surface of manifold plate 10 and the "POREX" sheet is punched through using a punch similar to that shown in FIG. 12. The result is a compacted column of chromatography media 90 in each well 14, held in its compacted condition by the "POREX" disk 88, as shown in FIG. 18. A number of such microchromatography manifold plates may be assembled together, one above the other, and sealed to each other by gasket 56 or 57 as previously described to allow for multistep isolation of a particular species. Alternatively a binding and washing cycle may be performed in one plate, with elution into a second plate containing a different medium, and the cycle repeated as needed.

The embodiments shown in FIGS. 15-18 may also include pins 45, 46 and 47 (not shown).

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. Microfiltration apparatus comprising:
   a manifold plate having an array of filtering wells for receiving liquid samples to be filtered;
   an array of planar bottom members, wherein each of said wells is closed at its bottom by one of said planar bottom members so as to provide a filter support surface for a filter medium;
   a filter disposed on said filter support surface; and
   at least one individual filtrate discharge nozzle in fluid communication with each of said filtering wells, each of said discharge nozzles depending from the bottom of each of said planar members at a point radially outward from the sidewall of the filtering well in communication therewith.

2. The apparatus of claim 1 wherein said manifold plate and said planar members are an integrally molded, single piece construction.

3. The apparatus of claim 1 wherein said planar members are integrally formed as a single piece filter support plate, sealed to said manifold plate around the bottom of each of said wells.

4. The apparatus of claim 1 wherein said filter support surface at the bottom of each of said filtering wells has at least one open channel in fluid communication with said at least one nozzle for collection of filtrate and delivery of the collected filtrate to the said at least one nozzle.

5. The apparatus of claim 3 wherein each of said filtering wells is defined by an open ended cylindrical member depending from the upper surface of said manifold plate and wherein a top planar surface of said filter support plate is provided with a plurality of recesses, equal in number to and aligned with said filtering wells, the lower ends of said cylindrical members being welded within said recesses.

6. The apparatus of claim 3 wherein each of said filtering wells is defined by an open ended cylindrical member depending from the upper surface of said manifold plate and wherein a top planar surface of said filter support plate is provided with a plurality of annular members, equal in number to and aligned with said filtering wells, the lower ends of said cylindrical members being press fit within said annular members.

7. The apparatus of claim 1 wherein said filter comprises a disc of filter medium sealed in the bottom of each of said filtering wells.

8. The apparatus of claim 2 wherein said filter comprises:
   a disc of filter medium in the bottom of each of said filtering wells; and additionally comprising
   an annual member press-fit within each of said filtering wells to seal the disc against the filter support surface.

9. The apparatus of claim 1 further comprising a multiwell plate having a plurality of collection wells corresponding to the number of and aligned with said filtering wells, said multiwell plate mating with the bottom of said manifold plate with each of said filtrate discharge nozzles engaging the inner sidewall of one of said aligned collection wells.

10. The microfiltration apparatus of claim 9, further comprising:
   a plurality of sets of pins, each set of pins depending from a one of said planar members at the bottom of one of said filtering wells, the pins of each set being arranged to engage the sidewall of one of said aligned collection wells of said multiwell plate thereby maintaining alignment between the closed-bottom wells of said manifold plate and the wells of said multiwell plate and wherein at least one pin of each of said set is said at least one filtrate discharge nozzle.

11. The microfiltration apparatus of claim 7 wherein said disc of filter medium is a microporous membrane.

12. Microfiltration apparatus in accordance with claim 10 wherein each of said sets of pins comprises at least two pairs of diametrically opposed pins.

13. Microchromatography apparatus comprising:
   a manifold plate having an array of filtering wells for receiving liquid samples;
   an array of planar bottom members, wherein each of said wells is closed at its bottom by one of said planar bottom members so as to provide a filter support surface for a filter medium;
   filter members within a plurality o said filtering wells, each of said filter members being sealed around its periphery to the walls of said wells and resting on said support surface;
   chromatography medium within said plurality of filtering wells and a porous disc sealed within each of said plurality of wells with said chromatography medium held in a compacted state between said porous disc and said filter member;
   at least one individual filtrate discharge nozzle in fluid communication with each of said filtering wells, each of said discharge nozzles depending from the bottom of each of sad planar members at a point radially outward from the sidewall of the filtering well in communication therewith; and
   fluid conduits providing said fluid communication between each filtering well and said at least one discharge nozzle in fluid communication therewith.

* * * * *